United States Patent [19]

Johnson

[11] Patent Number: 5,300,084

[45] Date of Patent: Apr. 5, 1994

[54] PNEUMOPERITONEUM NEEDLE

[75] Inventor: David S. Johnson, Stamford, Conn.

[73] Assignee: United States Surgical Corporation, Norwalk, Conn.

[21] Appl. No.: 980,502

[22] Filed: Nov. 23, 1992

[51] Int. Cl.⁵ .............................................. A61B 17/34
[52] U.S. Cl. .................................... 606/185; 606/167; 604/51; 604/52; 604/126; 604/239; 604/264; 604/272
[58] Field of Search ................... 128/747, 763; 604/51, 604/52, 53, 126, 163, 164, 169, 170, 171, 187, 239, 240, 246, 243, 177, 257, 264, 272, 280, 294; 606/185, 167

[56] References Cited

U.S. PATENT DOCUMENTS

| | | |
|---|---|---|
| 3,960,651 | 6/1976 | Kometani et al. . |
| 4,025,679 | 5/1977 | Denny . |
| 4,127,131 | 11/1978 | Vaillancourt ........................ 604/239 |
| 4,361,619 | 11/1982 | Forsten et al. . |
| 4,579,698 | 4/1986 | Meyering et al. ................. 210/493.2 |
| 4,675,017 | 6/1987 | Sato ..................................... 604/126 |
| 4,715,372 | 12/1987 | Philippbar et al. . |
| 4,758,225 | 7/1988 | Cox et al. . |
| 4,808,168 | 2/1989 | Warring . |
| 4,861,353 | 8/1989 | Wyss . |
| 4,902,423 | 2/1990 | Bacino . |
| 4,983,434 | 1/1991 | Sassa . |
| 5,006,109 | 4/1991 | Douglas et al. . |
| 5,104,381 | 4/1992 | Gresl . |

OTHER PUBLICATIONS

1988 Product Brochure of Burron Medical, Inc. of Bethlehem, Pa.

Primary Examiner—C. Fred Rosenbaum
Assistant Examiner—Noelle Kent Gring

[57] ABSTRACT

A pneumoperitoneum needle comprises a lumen defining a passageway through which pneumoperitoneum gases may pass to the peritoneal cavity, a handle mechanism attached to a proximal end portion of the lumen and a filtration unit housed within the handle mechanism for filtering the pneumoperitoneum gases to be passed through the lumen. The filtration unit preferably includes a hydrophobic filter fabricated from a polytetrafluoroethylene material having a pore size ranging in value from about 0.2 to 0.5 microns. In an alternative embodiment, the filtration unit is incorporated within the handle mechanism of a Veress-type needle.

28 Claims, 3 Drawing Sheets

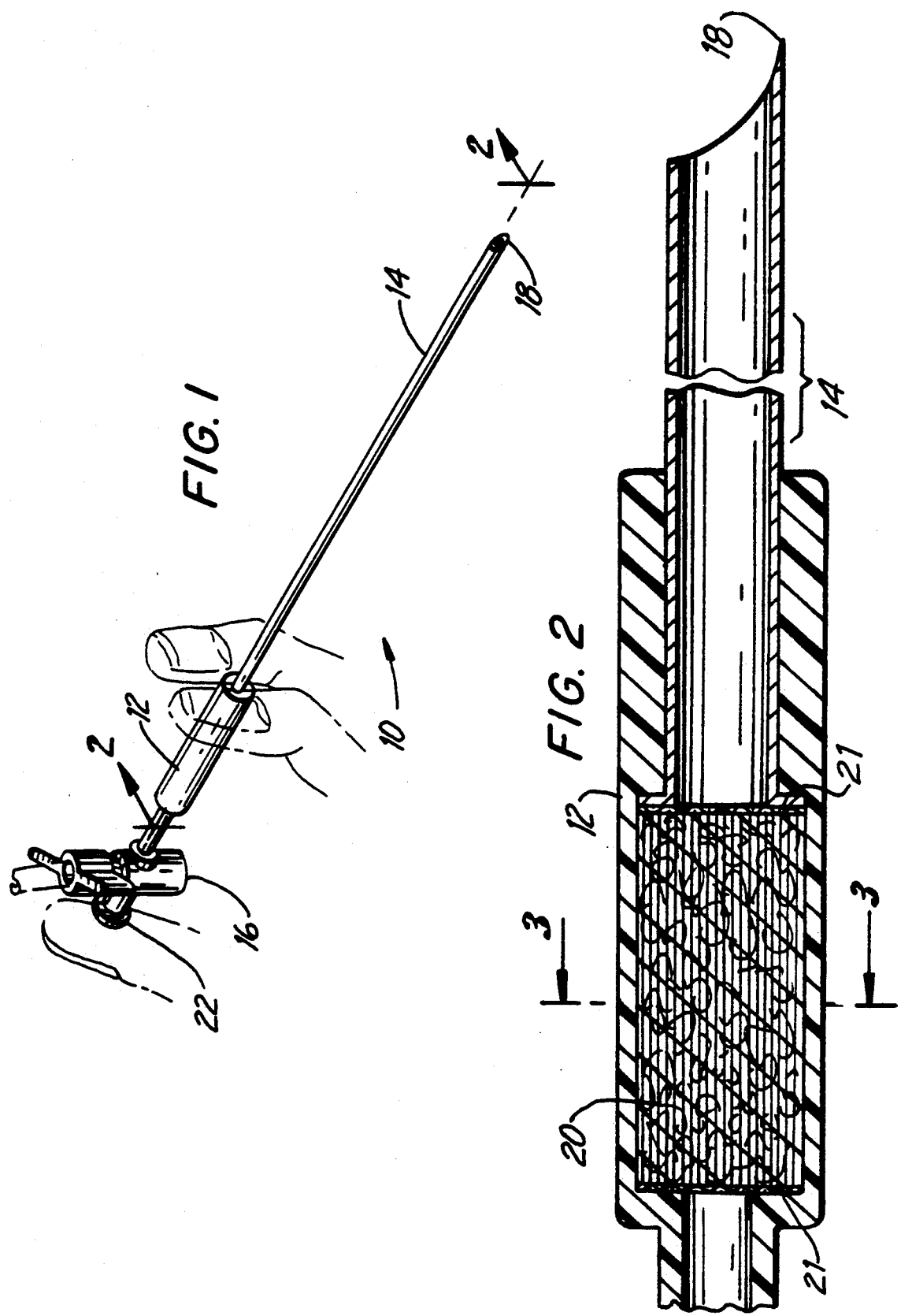

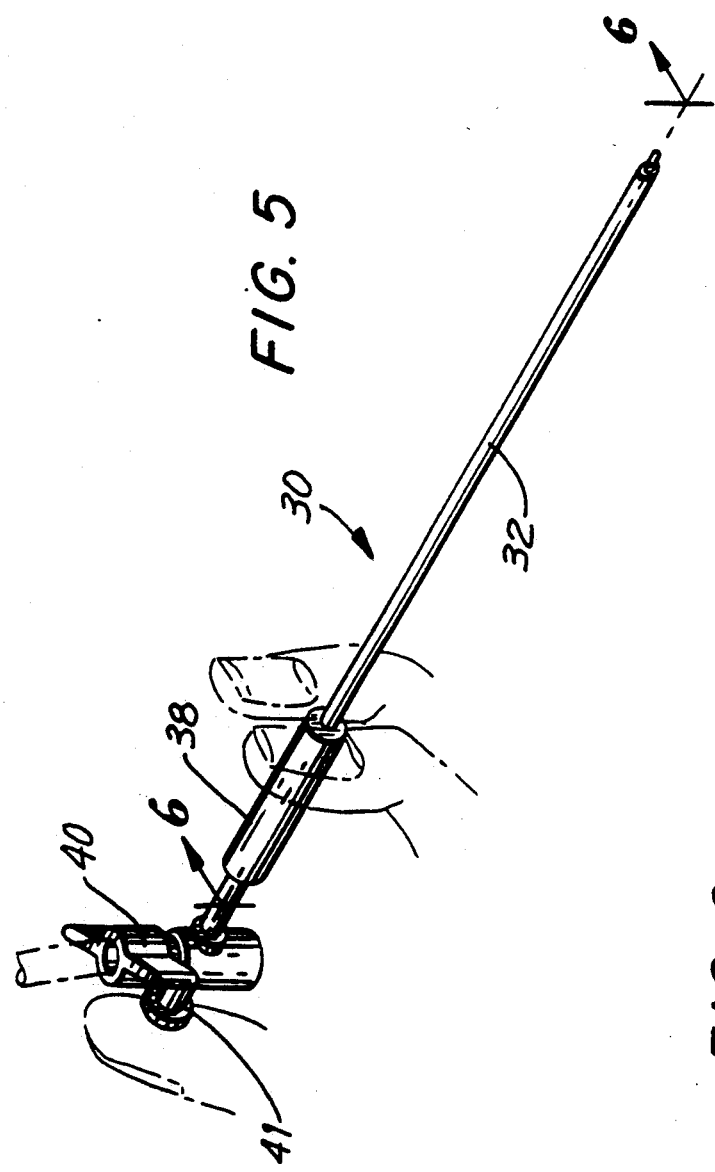
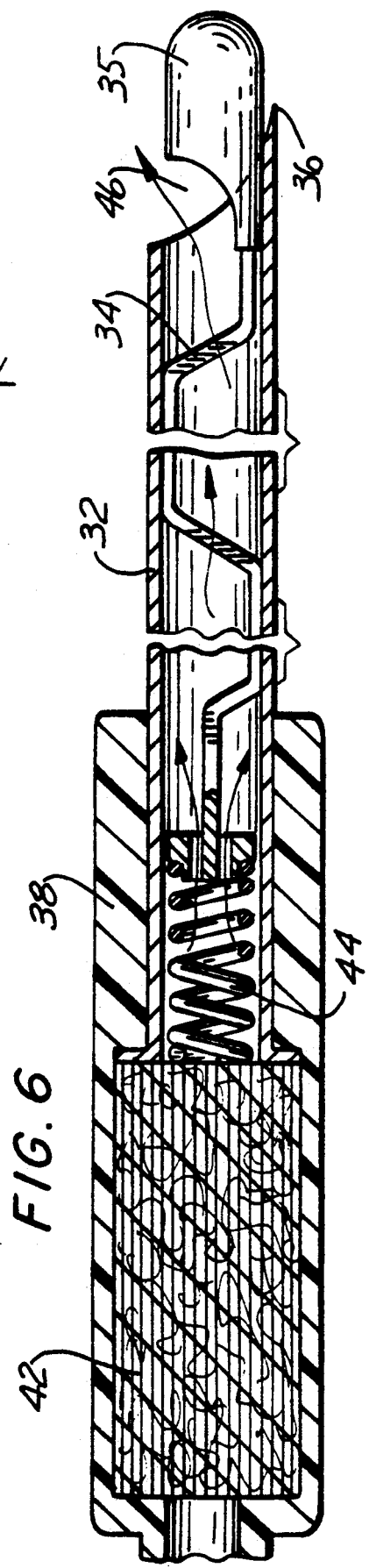

[## 5,300,084]

PNEUMOPERITONEUM NEEDLE

BACKGROUND OF THE INVENTION

1. Field of the Invention

This invention relates generally to a pneumoperitoneum needle for introducing gaseous fluids into a peritoneal cavity. More particularly, this invention is directed to a pneumoperitoneum needle featuring a built-in gas filtration unit.

2. Description of the Prior Art

Laparoscopic and endoscopic surgery has been widely accepted as the preferred surgical procedure for treatment of a variety of disorders that were formally treated with conventional surgical techniques.

In laparoscopic procedures, surgery is performed in the interior of the abdomen through a small incision; in endoscopic procedures, surgery is performed in any hollow viscus of the body through narrow endoscopic tubes inserted through small entrance wounds in the skin.

In conjunction with laparoscopic surgery, pneumoperitoneum gases are generally introduced into the peritoneal cavity to expand the cavity and raise the cavity wall away from the vital organs therein. Thereafter, a trocar, which is a sharp pointed instrument, is inserted into a cannula assembly and used to puncture the inner lining of the peritoneal cavity. The trocar is withdrawn and a laparoscopic surgical instrument is inserted through the cannula to perform the desired surgery.

A conventional system used for introducing the pneumoperitoneum gases into the peritoneal cavity includes a gas source or chamber and a pneumoperitoneum needle connected to the gas source via a flexible conduit. The pneumoperitoneum needle typically employed is a Veress-type needle which includes an elongated hollow outer sheath with a sharpened distal end for penetrating the inner lining of the peritoneal cavity. A spring-loaded blunt stylet is axially movable within the sheath and is distally biased so that the blunt end of the stylet extends beyond the sharp end of the needle once the needle penetrates the inner lining of the peritoneal cavity.

The pneumoperitoneum gas administering system also typically includes at least one volume flow regulator to control the rate of gas flow through the needle and a filtration unit to remove foreign matter from the gas such as water droplets or metal fragments inadvertently expelled from the gas source. The filtration unit is typically positioned between the gas source and the needle and is preferably replaced after a minimal number of uses.

A growing sentiment amongst medical personnel is that in order to provide optimal filtration of the pneumoperitoneum gases introduced into the peritoneal cavity and to adequately protect the patient from potential microbial contamination, the filtration unit should be replaced after a minimal number of uses, especially when $CO_2$ gas is used as the insufflating agent. However, with the administering systems known heretofore, the potential for non-replacement of the filtration unit remains relatively high since the filtration unit is an independently maintained component in the gas administering system whose replacement is usually dependent upon the judgment of a medical technician. Consequently, there exists the possibility that a clogged, inactivated or poorly effective filter may be used.

Therefore, it would be desirable to ensure replacement of a filter in a gas administering system after each use. The present invention addresses this need by providing a disposable pneumoperitoneum needle which includes a built-in filtration unit. Thus, after a laparoscopic procedure, the needle is disposed of along with the housed filtration unit, thereby insuring that a new filter is used in a subsequent procedure.

SUMMARY OF THE INVENTION

Generally stated, the present invention is directed to a needle for introduction of gaseous media into a body cavity, which comprises elongated means defining passageway means to direct gaseous media to the body cavity, holding means attached to a proximal end portion of the elongated means, and filter means associated with at least one of the holding means and elongated means for filtering the gaseous media prior to introduction into the passageway means.

The present invention is particularly directed to a pneumoperitoneum needle which comprises elongated means defining a passageway for introduction of pneumoperitoneum gaseous media into the peritoneal cavity, handle means attached to a proximal end portion of the elongated means and filter means associated with at least one of the handle means and the elongated means for filtering the pneumoperitoneum gaseous media to be passed through the elongated means. The elongated means includes a sharp piercing point at a distal end thereof to penetrate the inner lining of the peritoneal cavity. The filter means comprises a hydrophobic filter which is preferably fabricated from a polytetrafluoroethylene material having a pore size ranging in value from about 0.2 to 0.5 microns. In a preferred embodiment, the hydrophobic filter material contains a plurality of pleats. In another preferred embodiment, the hydrophobic filter is generally disc-shaped. The hydrophobic filter may also comprise a reinforcement mesh fabricated from polypropylene or polytetrafluorethylene to provide support to the filter.

The pneumoperitoneum needle further comprises valve means connected to a proximal end of the handle means for regulating flow of the pneumoperitoneum gaseous media through the elongated means.

In another preferred embodiment, the pneumoperitoneum needle comprises handle means having a proximal end and a distal end, an elongated sheath connected to the distal end of the handle means and defining a passageway through which pneumoperitoneum gases may pass to and from the peritoneal cavity, a stylet disposed within the passageway of the elongated sheath and longitudinally movable between a retracted position and an extended position, spring means attached to a proximal end of the stylet and housed within the handle means for biasing the stylet to the extended position and filter means housed within the handle means for filtering the pneumoperitoneum gases to be passed through the elongated sheath. The stylet includes a blunt end portion at a distal end thereof which extends beyond the sharp distal end of the elongated sheath when the stylet is in the extended position.

A method is also disclosed for introducing gaseous media to a body cavity with a pneumoperitoneum needle which permits passage of pneumoperitoneum gaseous media therethrough. The method comprises the steps of providing handle means having a built-in filtration unit at the proximal end portion of the needle, applying a distal force to the handle means so that a piercing end of the needle penetrates the inner lining of the peritoneal cavity and supplying pneumoperitoneum gaseous media through the handle means so that the filtration unit filters the gaseous media prior to passage through the needle and into the peritoneal cavity.

BRIEF DESCRIPTION OF THE DRAWINGS

Preferred embodiments of the invention are described hereinbelow with reference to the drawings wherein:

FIG. 1 is a perspective view of the pneumoperitoneum needle of the present invention;

FIG. 2 is an enlarged cross-sectional view taken along lines 2—2 of FIG. 1 illustrating the handle portion, the filtration unit housed within the handle portion and the piercing end of the needle;

FIG. 5 is a perspective view of another alternative embodiment of the pneumoperitoneum needle of the present invention;

FIG. 6 is an enlarged cross-sectional view taken along lines 6—6 of FIG. 5 illustrating the elongated sheath and the stylet disposed within, with the stylet being in the normal extended position.

DETAILED DESCRIPTION OF THE PREFERRED EMBODIMENTS

Figure 3:
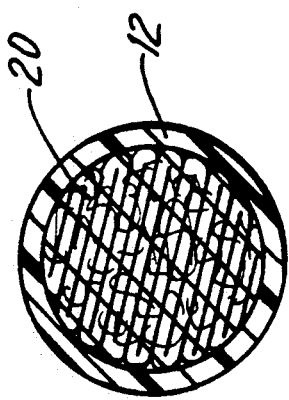
FIG. 3 is a cross-sectional view taken along the lines 3—3 of FIG. 2 further illustrating the housed filtration unit.

Referring to FIGS. 1-3, there is illustrated the preferred disposable pneumoperitoneum needle 10 constructed according to the present invention. Needle 10 serves as a conduit between the gas source of a pneumoperitoneum gas administering system and the peritoneal cavity so that the gases may enter and expand the peritoneal cavity to provide improved access to the internal organs therewithin during laparoscopic surgery.

Needle 10 includes handle 12, elongated sheath 14 connected to a forward end of the handle and valve 16 connected to the rear end of the handle. Handle 12 and valve 16 are each preferably fabricated from a polymeric material such as an acrylic, polystyrene, polycarbonate and styrene-acrylonitrile (SAN) copolymer. In a preferred embodiment, handle 12 and valve 16 are molded as a single unit. Sheath 14 is fabricated from a hardened biocompatible material such as stainless steel or titanium. Sheath 14 includes piercing edge 18 at a distal end thereof for penetrating the inner lining of the peritoneal cavity.

Valve 16 regulates the amount of pneumoperitoneum gases flowing through elongated sheath 14 and into the peritoneal cavity. Valve 16 may be any conventional valve suitable for this purpose such as a stop-cock valve. Valve 16 includes an inlet portion 22 to receive and connect a flexible conduit which carries the gas from the gas source to the needle destination.

As best shown in FIGS. 2 and 3, handle 12 includes pneumoperitoneum gas filter 20 housed within a circular channel defined within the handle. Filter 20 filters gas borne particles emanating from the gas source and conduit system to protect the patient from potential microbial contamination. Filter 20 is preferably pleated and extends across the full diameter of the channel to ensure complete filtration of the transmitted gases.

Filter 20 may be made from any material medically suitable with the gaseous fluids being introduced within the peritoneal cavity. When $CO_2$ gas is used as the insufflating agent, filter 20 is preferably a hydrophobic filter fabricated from a polytetrafluoroethylene (PTFE) material having a pore size ranging from about 0.2 microns to about 0.5 microns.

Filter 20 may include a non-fiber releasing polypropylene or polytetrafluorethylene mesh 21 to reinforce and provide upstream and downstream support for the filter. Mesh 21 may be a separate structure from filter 20 or in the alternative incorporated within the filter. Mesh 21 may be affixed at the proximal and/or distal end surfaces of the filter as shown.

Needle 10 may be inserted within a body cavity by grasping the needle with the thumb against the proximal end of valve 16 and the index and middle fingers against the forward edge of handle 12, as shown in phantom in FIG. 1. Thereafter, a distal force is applied to the needle to pierce the inner lining of the peritoneal cavity. The gas conduit from the gas source is then connected to inlet portion 22 of valve 16 and the valve is opened to provide gas flow through sheath 14 and into the peritoneal cavity to expand the cavity to a predetermined pressure. The needle is removed and disposed of, and the surgery is completed. The disposability of the pneumoperitoneum needle eliminates the possibility that a clogged, inactivated or fully ineffective filter in a subsequent laparoscopic procedure is used, the possibility to which conventional systems are subject.

Figure 4:
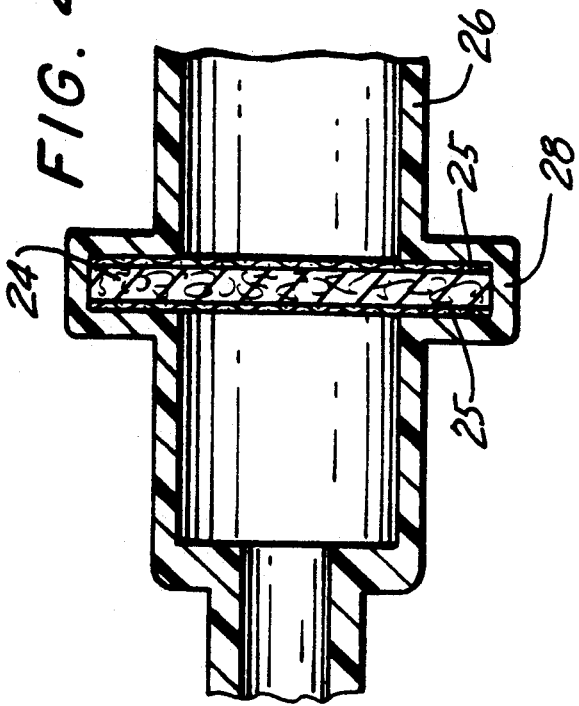
FIG. 4 is a cross-sectional view of an alternative embodiment of the present invention incorporating a disc-shaped filtration unit housed within the handle portion.

FIG. 4 illustrates an alternative embodiment of the pneumoperitoneum needle of the present invention. In this embodiment, filter 24 is generally disc-shaped and is housed within collar 28 of handle 26. The filter specifications are preferably identical to filter 20 of the embodiment of FIG. 1, i.e. a hydrophobic filter material of polytetrafluoroethylene (PTFE) having a pore size of 0.2-0.5 microns. The diameter of filter 24 is preferably about 2.5 cms. A polypropylene or polytetrafluoroethylene support mesh 25 may be affixed to the end surfaces of filter 24 or incorporated within the filter as previously described.

Figure 7:
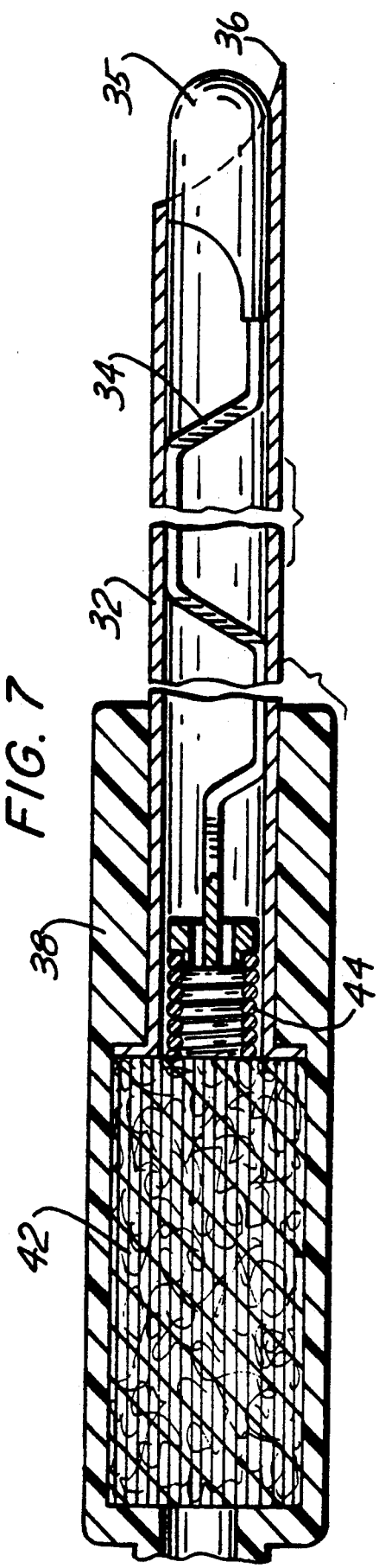
FIG. 7 is an enlarged cross-sectional view similar to the view of FIG. 6 illustrating the stylet in the retracted position.

Referring now to FIGS. 5-7, there is illustrated another alternative embodiment of the pneumoperitoneum needle of the present invention. Pneumoperitoneum needle 30 is a Veress-type needle and includes an elongated sheath 32 having stylet 34 disposed within the sheath. Sheath 32 is similar in construction to the sheath described in the embodiment of FIG. 1 and includes piercing tip 36. Handle 38, stop-cock valve 40, and filter 42 are also similar in construction to their corresponding components described in the embodiment of FIG. 1.

Stylet 34 is adapted for reciprocal longitudinal movement from an extended position as shown in FIG. 6 to a retracted position as shown in FIG. 7, and is biased to the extended position under the influence of coil spring 44. Spring 44 is affixed to the proximal end of stylet 34 and is also affixed, by conventional means, within the interior of handle 38 adjacent filter 42. Stylet 34 has a blunt end 35 at its distal end which extends beyond the distal end of sheath 32 when the stylet is in its extended position. As shown in FIG. 6, an opening 46 between blunt end 35 and piercing end 36 of sheath 32 permits release of the pneumoperitoneum gases communicating through the sheath.

In use, needle 30 is applied against the patient's abdominal area. Blunt end 35 of stylet 34 initially engages the cavity wall thereby forcing the stylet to assume its retracted position (FIG. 7) which exposes piercing tip 36 of sheath 32. Distal force is applied to needle 30 so that tip 36 penetrates the inner lining of the peritoneal cavity. Once the cavity is penetrated, stylet 34 moves forwardly to its normal extended position under the influence of coil spring 44. In this position, blunt end 35 extends beyond piercing end 36 of sheath 32 (FIG. 6) to prevent puncture or laceration of inner abdominal structures. The conduit is connected to inlet opening 41 of valve 40 and the valve is opened to permit the pneumoperitoneum gases to flow through sheath 32 and out opening 46 (as shown by the arrows) to enter into the peritoneal cavity.

The disposable pneumoperitoneum needle of the present invention, which possesses its own built-in filtration unit, eliminates the possibility that a clogged, inactivated or poorly effective filter may be used in a subsequent laparoscopic procedure.

Although the present invention has been described in terms of preferred embodiments, it is to be understood that the invention is not limited to the precise embodiments illustrated and that various other changes and modifications may be effected therein by one skilled in the art without departing from the scope of the invention.

What is claimed is:

1. A needle for introduction of gaseous media into a body cavity, which comprises:
   elongated means defining passageway means to direct gaseous media to the body cavity;
   holding means attached to a proximal end portion of said elongated means; and
   filter means associated with at least one of said holding means and elongated means for filtering the gaseous media prior to introduction into said passageway means.

2. A pneumoperitoneum needle, which comprises:
   elongated means defining a passageway for introduction of pneumoperitoneum gaseous media into the peritoneal cavity;
   handle means attached to a proximal end portion of said elongated means; and
   filter means associated with at least one of said handle means and said elongated means for filtering the pneumoperitoneum gaseous media to be passed through said elongated means.

3. The pneumoperitoneum needle according to claim 2 wherein said filter means comprises a hydrophobic filter.

4. The pneumoperitoneum needle according to claim 3 wherein said hydrophobic filter comprises a polytetrafluoroethylene material.

5. The pneumoperitoneum needle according to claim 4 wherein said polytetrafluoroethylene material has a pore size ranging in value from about 0.2 to 0.5 microns.

6. The pneumoperitoneum needle according to claim 5 wherein said hydrophobic filter material contains a plurality of pleats.

7. The pneumoperitoneum needle according to claim 5 wherein said hydrophobic filter is generally disc-shaped.

8. The pneumoperitoneum needle according to claim 7 wherein the diameter of said hydrophobic filter is approximately 2.5 cm.

9. The pneumoperitoneum needle according to claim 2 wherein said elongated means includes a sharp piercing point at a distal end thereof to penetrate the inner lining of the peritoneal cavity.

10. The pneumoperitoneum needle according to claim 2 further comprising valve means connected to a proximal end of said handle means for regulating flow of the pneumoperitoneum gaseous media through said elongated means.

11. The pneumoperitoneum needle according to claim 3 wherein said hydrophobic filter comprises a reinforcement mesh for providing additional support to said filter.

12. The pneumoperitoneum needle according to claim 11 wherein said reinforcement mesh is fabricated from a material selected from the group consisting of polypropylene and polytetrafluoroethylene.

13. A pneumoperitoneum needle, which comprises:
   handle means having a proximal end and a distal end;
   an elongated sheath connected to said distal end of said handle means and defining a passageway through which pneumoperitoneum gases may pass to and from the peritoneal cavity;
   a stylet disposed within said passageway of said elongated sheath and longitudinally movable between a retracted position and an extended position, said stylet including a blunt end portion at a distal end thereof, said blunt end portion extending beyond said distal end of said elongated sheath when said stylet is in said extended position;
   spring means attached to a proximal end of said stylet and housed within said handle means for biasing said stylet to said extended position; and
   filter means housed within said handle means for filtering the pneumoperitoneum gases to be passed through said elongated sheath.

14. The pneumoperitoneum needle according to claim 13 wherein said filter means comprises a hydrophobic filter.

15. The pneumoperitoneum needle according to claim 14 wherein said hydrophobic filter comprises a polytetrafluoroethylene material.

16. The pneumoperitoneum needle according to claim 15 wherein said polytetrafluoroethylene material has a pore size ranging in value from about 0.2 to 0.5 microns.

17. The pneumoperitoneum needle according to claim 16 wherein said hydrophobic filter material contains a plurality of pleats to provide an effective filtration area greater than the cross-sectional area of said filter.

18. The pneumoperitoneum needle according to claim 16 wherein said hydrophobic filter is generally disc-shaped.

19. The pneumoperitoneum needle according to claim 18 wherein the diameter of said hydrophobic filter is approximately 2.5 cm.

20. The pneumoperitoneum needle according to claim 13 wherein said elongated means includes a sharp piercing point at a distal end thereof to penetrate the inner lining of the peritoneal cavity.

21. The pneumoperitoneum needle according to claim 13 further comprising valve means connected to said proximal end of said handle means for regulating flow of the pneumoperitoneum gases through said elongated sheath.

22. In combination with a conduit through which gaseous fluids may be passed to and from a body cavity:

housing means attached to a proximal end portion of the conduit; and filter means housed within said housing means for filtering the gaseous fluids to be introduced into the body cavity.

23. The combination of claim 22 wherein said filter means is a pleated filter.

24. The combination of claim 22 wherein said housing means is adapted and configured to house said pleated filter.

25. The combination of claim 22 wherein said filter means is a disc-shaped filter.

26. The combination of claim 25 wherein said housing means is adapted and configured to house said disc-shaped filter.

27. A pneumoperitoneum needle, which comprises:

lumen means defining a passageway through which pneumoperitoneum gases may pass to and from the peritoneal cavity;

handle means attached to a proximal end portion of said lumen means; and filter means housed within said handle means for filtering the pneumoperitoneum gases to be passed through said lumen means.

28. A method for introducing gaseous media to a body cavity through a pneumoperitoneum needle which permits passage of pneumoperitoneum gaseous media therethrough, comprising:

providing handle means at the proximal end portion of said needle, said handle means adapted and configured for holding said needle and for housing filter means for filtering the pneumoperitoneum gaseous media prior to passage through said needle;

applying a distal force to said handle means so that a piercing end of said needle penetrates the inner lining of the peritoneal cavity; and supplying the pneumoperitoneum gaseous media through said handle means so that said filter means filters the gaseous media prior to passage through said needle and into the peritoneal cavity.

* * * * *